United States Patent [19]

Newton et al.

[11] Patent Number: 5,062,882

[45] Date of Patent: Nov. 5, 1991

[54] TRIAZINE HERBICIDES

[75] Inventors: Trevor W. Newton, Sittingbourne; Alastair McArthur, Oare, both of England

[73] Assignee: Shell International Research Maatschappij B. V., Netherlands

[21] Appl. No.: 324,440

[22] Filed: Mar. 16, 1989

[30] Foreign Application Priority Data

Apr. 7, 1988 [GB] United Kingdom ............... 8808071

[51] Int. Cl.⁵ ................. A01N 43/66; A01N 43/68; C07D 251/46; C07D 251/52
[52] U.S. Cl. .................................... 71/93; 544/211; 544/197; 544/219; 544/206; 544/208; 544/113; 544/218; 544/83; 544/212; 544/198; 544/207; 544/209; 71/90
[58] Field of Search ............... 71/93, 90; 544/211, 544/197, 219, 206, 208, 113, 218, 83, 212, 198, 207, 209

[56] References Cited

U.S. PATENT DOCUMENTS

| | | | |
|---|---|---|---|
| 2,891,855 | 6/1959 | Gysin et al. | 71/74 |
| 3,505,325 | 4/1970 | Schwarze | 544/204 |
| 3,620,710 | 11/1971 | Schwarze | 71/93 |
| 3,629,259 | 12/1971 | Schwarze | 544/204 |
| 4,770,691 | 9/1988 | Nezu et al. | 71/92 |

FOREIGN PATENT DOCUMENTS 63-258467 10/1988 Japan .

OTHER PUBLICATIONS

Pandya, K. S., et al., J. Inst. Chemists (India), XLVIII(5), 245-247 (1976).
Pandya, K. S., et al., J. Inst. Chemists (India), vol. 52(1), pp. 7-8 (1/80).

Primary Examiner—John M. Ford

[57] ABSTRACT

Triazine herbicides of the general formula I

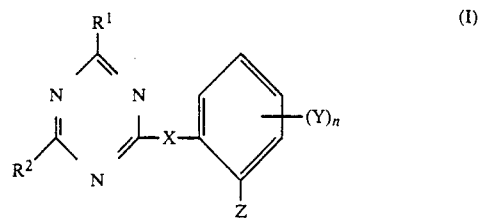

wherein
$R^1$ and $R^2$ each independently represent a hydrogen or halogen atom, or an optionally substituted alkyl, alkenyl, alkynyl, cycloalkyl, alkoxy, alkenyloxy, alkynyloxy, aryloxy, alkylthio, alkenylthio, alkynylthio, arylthio or amino group, or a formyl, optionally substituted alkylcarbonyl, cyano, carboxy, optionally substituted alkoxycarbonyl, dialkylaminoxy, dialkyliminoxy or azido group;
X represents an oxygen or sulphur atom or a group —SO₂—, —SO—, or —NR⁴—where R⁴ represents a hydrogen atom or an optionally substituted alkyl group;
n is an integer from 1 to 4;
Y represents a hydrogen atom or the or each Y each independently represents a halogen atom, a hydroxy group or an optionally substituted alkyl, alkenyl, alkynyl, aryl alkoxy, alkenyloxy, alkynyloxy, aryloxy, heterocyclyloxy, alkylthio, alkenylthio, alkynylthio, arylthio or amino group, or a formyl, optionally substituted alkylcarbonyl, cyano or nitro group, or, when n is at least 2, two groups Y may be linked to form a fused saturated or unsaturated carbocylic or heterocyclic ring; and
Z represents a hydroxyalkyl, hydroxybenzyl, or mono—, di—or trialkoxyalkyl group, a group —CH=NOH, or an optionally esterified carboxyalkyl group, or a group COR³ where R³ represents a hydrogen or halogen atom, or a hydroxy group, or an optionally substituted alkyl, aryl, alkenyl, alkynyl, alkoxy, alkenyloxy, alkynyloxy, cycloalkyloxy, aryloxy, dialkylaminoxy, dialkyliminoxy, amino, alkylthio, arylthio, alkenylthio or alkynylthio group, or R³ represents a group —OR⁵ where R⁵ represents an optionally substituted heterocyclic ring; or a carboxylic acid salt of a compound of general formula I with an equivalent amount of an inorganic or organic cation, together with at least one carrier.

9 Claims, No Drawings

TRIAZINE HERBICIDES

This invention relates to triazine herbicides, their preparation and use.

Herbicidal compounds comprising a 2,4,6-substituted-1,3,5-triazine ring are well known, for example from UK Patent No. 814947 which describes herbicidal compositions comprising certain 6-chloro-1,3,5-triazine-2,4-diamines and UK Patent No. 1132306 which describes certain 6-substituted 1,3,5-triazine 2,4-diamines, one of the amino groups having cyanoalkylamino substitution.

Certain substituted phenoxy (s)triazines are disclosed in the literature, i.e. J. Inst. Chemists (India), 1976, 48(5), 245 to 247, and J. Inst. Chemists (India), 1980, 52(1), 7 and 8, and are shown to have antibacterial activity.

We have now found a class of 2-substituted 1,3,5-triazines which exhibit useful herbicidal activity.

In accordance with the present invention there is provided a herbicidal composition which comprises a compound of the general formula I

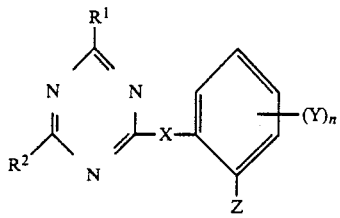

wherein $R^1$ and $R^2$ each independently represent a hydrogen or halogen atom, or an optionally substituted alkyl, alkenyl, alkynyl, cycloalkyl, alkoxy, alkenyloxy, alkynyloxy, aryloxy, alkylthio, alkenylthio, alkynylthio, arylthio or amino group, or a formyl, optionally substituted alkylcarbonyl, cyano, carboxy, optionally substituted alkoxycarbonyl, dialkylaminoxy, dialkyliminoxy or azido group;

X represents an oxygen or sulphur atom or a group —$SO_2$—, —SO—, or —$NR^4$— where $R^4$ represents a hydrogen atom or an optionally substituted alkyl group;

n is an integer from 1 to 4;

Y represents a hydrogen atom or the or each Y each independently represents a halogen atom, a hydroxy group, or an optionally substituted alkyl, alkenyl, alkynyl, aryl, alkoxy, alkenyloxy, alkynyloxy, aryloxy, alkylthio, alkenylthio, alkynylthio, arylthio or amino group, or a formyl, optionally substituted alkylcarbonyl, cyano or nitro group, or, when n is at least 2, two groups Y may be linked to form a fused saturated or unsaturated carbocyclic or heterocyclic ring; and Z represents a hydroxyalkyl, hydroxybenzyl, or mono—, di— or trialkoxyalkyl group, a group —CH=NOH, or an optionally esterified carboxyalkyl group, or a group $COR^3$ where $R^3$ represents a hydrogen or halogen atom, or a hydroxy group, or an optionally substituted alkyl, aryl, alkenyl, alkynyl, alkoxy, alkenyloxy, alkynyloxy, cycloalkyloxy, aryloxy, dialkylaminoxy, dialkyliminoxy, amino, alkylthio, arylthio, alkenylthio or alkynylthio group, or $R^3$ represents a group —$OR^5$ where $R^5$ represents an optionally substituted heterocyclic ring; or a carboxylic acid salt of a compound of general formula I with an equivalent amount of an inorganic or organic cation, together with at least one carrier.

Optional substituents for alkyl, alkenyl, alkynyl, alkoxy, alkenyloxy, alkynyloxy, alkylthio, alkenylthio, alkynylthio, alkylcarbonyl or alkoxycarbonyl groups may be independently selected from one or more of halogen atoms and alkoxy, hydroxy, alkylthio, arylthio, aryl, alkylsulphonyl, alkylsulphinyl, alkylenedioxy, alkylenedithio, haloalkyl and alkoxycarbonyl groups, heterocyclic groups, and dialkyliminoxy, optionally substituted amino, trialkylsilyl, alkylcarbonyl, arylcarbonyl, alkoxycarbonyl, carboxy, cyano, thiocyanato and optionally substituted aminocarbonyl groups.

Optional substituents for aryl, cycloalkyl aryloxy or arylthio groups or heterocyclic rings may be independently selected from one or more of halogen atoms and nitro, cyano, alkyl, haloalkyl, alkoxy alkylthio, alkoxycarbonyl and aralkoxycarbonyl groups.

Optional substituents for an amino group may be independently selected from alkyl, alkoxy, amino, mono or dialkylamino, arylamino, alkoxyalkyl, haloalkyl, hydroxy, hydroxyalkyl, carboxyalkyl or alkylcarbonylamino, or the amino group may form part of a heterocyclic ring.

Carboxylic acid salts of the compounds of general formula I include salts with inorganic cations derived from alkali metals, alkaline earth metals and transition metals and with organic cations such as alkylammonium and alkylsulphonium cations.

Alkyl groups preferably have 1 to 12 carbon atoms, especially 1 to 6 carbon atoms, while alkenyl and alkynyl groups preferably have 2 to 12 carbon atoms, especially 2 to 6 carbon atoms. Cycloalkyl groups preferably have 3 to 8 carbon atoms.

When halogen is the optional substituent, the group is suitably substituted by 1 to 3 halogen atoms, preferably selected from fluorine and chlorine.

$R^1$ and $R^2$ in formula I are preferably each independently selected from $C_{1-4}$ alkyl groups, especially methyl, $C_{2-4}$ alkynyloxy groups, especially propargyloxy, $C_{1-4}$ alkoxy groups, especially methoxy and ethoxy, $C_{1-4}$ haloalkoxy groups, $C_{1-4}$ alkylthio groups, especially methylthio, substituted amino groups, especially mono and dimethylamino, mono and diethylamino, mono and dimethoxyamino, dimethylhydrazino and N-methoxy-N-methylamino and dialkyliminoxy groups, especially dimethylaminoxy.

X is preferably an oxygen or sulphur atom.

Z preferably represents a group $COR^3$ where $R^3$ represents a hydrogen atom or a $C_{1-4}$ alkoxy group, preferably methoxy or ethoxy, a $C_{1-4}$ alkylthio group, for example, n or -i-propylthio, a $C_{2-4}$ alkenyloxy group, for example vinyloxy, or a hydroxy, phenoxy phenylthio, or benzyloxy group, a substituted $C_{1-4}$ alkoxy group, for example ethoxyethoxy or thienylmethoxy, a halosubstituted phenoxy group, or a dialkyliminoxy, preferably dimethyliminoxy, or Z represents a hydroxy or alkoxy substituted alkyl group.

n is preferably 1 and Y preferably represents a hydrogen atom or a halogen atom, preferably chlorine, or a $C_{1-4}$ alkyl group, preferably methyl, or a $C_{1-4}$ alkoxy or alkenyloxy group, or a benzyloxy group, a nitro group, or an amino or substituted amino group. Alternatively, when n is 2, two groups Y may be linked to form a fused ring system, eg. a naphthyl ring system.

Preferred carboxylic acid salts of the compounds of general formula I include sodium salts.

The compounds of general formula I may be prepared by reacting a compound of general formula II

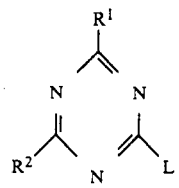

where $R^1$ and $R^2$ are as defined above and L represents a leaving group, preferably a halogen atom, especially chlorine, under basic conditions with a compound of general formula III

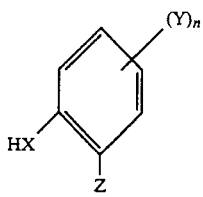

where Y, X, n and Z are as defined above, followed optionally by conversion of the resulting compound of general formula I to another compound of general formula I, or by conversion of a carboxylic acid of general formula I into a salt thereof or conversion of a carboxylic acid salt of a compound of general formula I into the free acid or into another salt.

The basic conditions may suitably be provided, for example, by the presence of an alkali metal, such as metallic sodium or potassium, an alkali metal hydride, such as sodium or potassium hydride, an alkaline earth metal hydride, such as calcium hydride, an alkali metal carbonate or bicarbonate, such as sodium or potassium carbonate or sodium bicarbonate, an alkali metal alkoxide, such as potassium t-butoxide, an alkali metal hydroxide, such as sodium or potassium hydroxide, or a tertiary amine, such as triethylamine, pyridine or 1,8-diazabicyclo[5.4.0] undec-7-ene.

The reaction is suitably carried out in an inert organic solvent such as a hydrocarbon solvent, eg. benzene or toluene, a chlorinated hydrocarbon, eg. dichloromethane or chloroform, an alcohol, eg. methanol or ethanol, an ether, eg. diethyl ether, tetrahydrofuran, 1,4-dioxane, a ketone, eg. acetone or methyl ethyl ketone, an ester, eg. ethyl acetate, an aprotic polar solvent, eg. dimethylformamide, dimethylacetamide or dimethylsulphoxide or a nitrile, eg. acetonitrile, or in water, with appropriate selection of the agent generating the basic conditions for the reaction.

The reaction may be carried out over a wide temperature range, for example from 0° C. to the refluxing temperature of the solvent employed.

The amounts of reactants II and III can vary suitably within the range of 0.1 to 10 moles of II per mole of III. However substantially equivalent amounts of II and III are preferably employed.

The compound of general formula I obtained by the above described method may readily be converted to a further compound of general formula I by methods known to a man skilled in the art. Thus for example, a compound of general formula I where $R^1$ and/or $R^2$ represents a halogen atom, suitably chlorine, may be reacted with an amine, such as dimethylamine, to displace the or each halogen to give the corresponding compound of formula I in which $R^1$ and/or $R^2$ represents a substituted amino group. Likewise a compound of general formula I in which $R^1$ and/or $R^2$ represents a halogen atom, may be reacted with an alkylthio organometallic compound, for example sodium methanethiolate, to yield the corresponding compound of general formula I in which $R^1$ and/or $R^2$ represents an alkylthio group such as methylthio, or may be hydrogenated to yield the corresponding compound in which $R^1$ and/or $R^2$ is a hydrogen atom. Compounds of general formula I in which Z represents an ester group may be hydrolysed by methods well known in the art to yield acids of formula I. Alternatively, hydrogenation of, for example, the benzyl ester of formula I can be employed to yield acids of formula I. Compounds of general formula I in which X represents a sulphur atom may be oxidised to compounds of general formula I in which X represents a sulphonyl or sulphoxide linkage. Similarly compounds of general formula I in which X represents a group —NH— may be alkylated to compounds of general formula I in which X represents a group —NR$^4$— wherein R$^4$ is other than hydrogen.

Acid and salt conversion reactions may be carried out using conventional methods as appropriate.

The prepared compound of general formula I may, if desired, be isolated and purified using conventional techniques.

Many of the starting triazine compounds of general formula II are known or can be prepared using techniques described in the literature. For example such compounds may be prepared from the 2,4,6-trichloro-triazine by methods such as those described by Dudley et al, J. Am. Chem. Soc., 73, 2986, (1951), Koopman et al, Rec. Trav. Chim., 79, 83, (1960), Hirt et al, Helv. Chim. Acta, 33, 1365, (1950), Kobe et al, Monatshefte fur Chemie, 101, 724, (1970) and Ross et al, U.S. Pat. No. 3 316 263.

The compounds of general formula III are also either known compounds or can be prepared using techniques described in the literature, for example using the general techniques described in Annalen der Chemie, 113, 125 (1860).

The present invention also provides a compound of the general formula I wherein $R^1$, $R^2$, X, n, Y and Z are as defined above with the proviso that when $R^1$ represents a 4-chloroanilino group, $R^2$ does not represent a substituted amino group.

The preferred meanings of $R^1$, $R^2$, X, n, Y and Z in compounds of the present invention are those indicated above as being preferred in relation to the herbicidal compositions of the present invention.

Compounds of the general formula I have been found to have interesting activity as herbicides having a wide range of pre- and post-emergence activity against undesirable species.

The present invention further provides the use of a composition or a compound according to the invention as a herbicide.

Further, in accordance with the invention there is provided a method of combating undesired plant growth at a locus by treating the locus with a composition or compound according to the invention. The locus may, for example, be the soil or plants in a crop area. Application to the locus may be pre-emergence or post-emergence. The dosage of active ingredient used may, for example, be from 0.01 to 10 kg/ha, preferably 0.05 to 4 kg/ha.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating herbicidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ether; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example, the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% W of active ingredient and usually contain in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–75% w active ingredient and 0–10% w of additives such as stabilisers, surfactants, slow release modifiers and binding agents. The so-called "dry flowable powders" consist of relatively high concentration of active ingredient. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

The composition of the invention may also contain other ingredients, for example other compounds possessing herbicidal, insecticidal or fungicidal properties.

The invention will now be further described with reference to the accompanying Examples.

EXAMPLE 1

Methyl 2-(4,6-dimethoxy-1,3,5-triazin-2-yl)oxy benzoate

A mixture of 2-chloro-4,6-dimethoxytriazine (1.93 g), methyl salicylate (1.52 g) and potassium carbonate (1.79 g) in dry methyl ethyl ketone (60 ml) was refluxed for 4 hours. The mixture was cooled and the methyl ethyl ketone removed in vacuo. Water (100 ml) was added and the product was extracted into ether. The organic phase was dried using anhydrous magnesium sulphate and evaporated to give a product which crystallised on standing to give the title compound (2.9 g); mp 75.7° C.

Analysis (%): Calc. C 53.6, H 4.5, N 14.4. Found C 52.8, H 4.6, N 14.5.

EXAMPLE 2

Methyl 2-(4-chloro-6-methoxy-1,3,5-triazin-2-yl)oxy benzoate

A mixture of 2,4-dichloro-6-methoxytriazine (9.0 g), methyl salicylate (7.6 g) and potassium carbonate (6.93 g) in methyl ethyl ketone (200 ml) was refluxed for 2 to 3 hours. The solvent was removed in vacuo, water (150 ml) added and the product extracted into ether. The organic phase was dried using anhydrous magnesium sulphate and evaporated to give a product (12 g) which, after recrystallisation from hexane - ethyl acetate, gave the title compound; mp 97.5° C.

Analysis (%): Calc. C 48.7, H 3.4, N 14.2. Found C 49.0, H 3.6, N 14.2.

EXAMPLE 3

Methyl 2-(4-dimethylamino-6-methoxy-1,3,5-triazin-2-yl)oxy benzoate

Excess dimethylamine (about 2 ml) was added to a stirred solution of methyl 2-(4-chloro-6-methoxy-1,3,5-triazin-2-yl)oxy benzoate (3.0 g)(prepared as described in Example 2) in acetone (50 ml) at 0° C. A white precipitate formed. Stirring was continued for 1 hour, after which the solvent was evaporated and the resulting mixture partitioned between water and ether. The organic phase was dried using anhydrous magnesium sulphate and evaporated in vacuo. Flash chromatography (eluant hexane/ethyl acetate 70:30) was used to yield the title compound (1.36 g) as an oil.

Analysis (%): Calc. C 55.3, H 5.3, N 18.4. Found C 55.1, H 5.4, N 17.6.

EXAMPLE 4

Methyl 2-(4-methoxy-6-methylthio-1,3,5-triazin-2-yl)oxy benzoate

Sodium methanethiolate (0.7 g) was added to a stirred solution of methyl 2-(4-chloro-6-methoxy-1,3,5-triazin-2-yl)oxy benzoate (prepared as described in Example 2) (3.0g) in methyl ethyl ketone (50 ml). The reaction mixture was stirred and heated under reflux for 1 hour. After cooling the mixture was poured into water, extracted with dichloromethane, dried over anhydrous magnesium sulphate and chromatographed on silica gel, using as eluants dichloromethane followed by 5% ethyl acetate/dichloromethane to yield the title compound (1.4 g) m.p. 83.5° C.

Analysis (%): Calc. C 50.8, H 4.3, N 13.7. Found C 51.2, H 4.4, N 13.6.

The following further compounds of general formula I set out in Table 1 below were made using similar methods to those described in Examples 1 to 4 above.

TABLE 1

(I')

| Example | $R^1$ | $R^2$ | X | Z | Y | mp (°C.) | Analysis (%) (Calc. Found) C | H | N |
|---|---|---|---|---|---|---|---|---|---|
| 5 | OMe | OEt | O | $CO_2Me$ | H | oil | 55.1 / 55.3 | 5.0 / 5.2 | 13.8 / 13.3 |
| 6 | OMe | NHMe | O | $CO_2Me$ | H | 122.4 | 53.3 / 53.8 | 4.8 / 5.0 | 19.3 / 18.7 |
| 7 | OMe | Me | O | $CO_2Me$ | H | 76.6 | 56.7 / 56.3 | 4.7 / 4.6 | 15.3 / 15.2 |
| 8 | Cl | Me | O | $CO_2Me$ | H | 85.7 | 51.5 / 51.4 | 3.6 / 3.7 | 15.0 / 15.0 |
| 9 | Cl | Cl | O | $CO_2Me$ | H | 108.5 | 44.0 / 44.3 | 2.3 / 2.6 | 14.0 / 13.9 |
| 10 | OEt | OEt | O | $CO_2Me$ | H | oil | 56.4 / 56.3 | 5.4 / 5.4 | 13.2 / 13.2 |
| 11 | $NMe_2$ | $NMe_2$ | O | $CO_2Me$ | H | 91.9 | 56.8 / 56.8 | 6.0 / 6.1 | 22.1 / 22.2 |
| 12 | OMe | OMe | O | CHO | H | 97.8 | 55.2 / 55.3 | 4.2 / 4.4 | 16.1 / 16.0 |
| 13 | MeO | MeO | O | $CO_2Et$ | H | 60.7 | 55.1 / 55.2 | 4.9 / 5.0 | 13.8 / 13.9 |
| 14 | MeO | MeO | O | $CO_2Ph$ | H | 131.7 | 61.2 / 61.1 | 4.3 / 4.4 | 11.9 / 11.5 |
| 15 | MeO | MeO | O | $CO_2Me$ | 3-Me | 99.0 | 55.1 / 55.2 | 4.9 / 4.8 | 13.8 / 13.8 |
| 16 | MeO | MeO | O | $CO_2Me$ | 4-Me | 89.1 | 55.1 / 54.6 | 4.9 / 4.8 | 13.8 / 13.5 |
| 17 | MeO | MeO | O | $CO_2Me$ | 5-Me | oil | 55.1 / 54.9 | 4.9 / 5.2 | 13.8 / 13.0 |
| 18 | MeO | MeO | S | $CO_2Me$ | H | 87.3 | 50.8 / 49.8 | 4.2 / 4.2 | 13.7 / 13.3 |
| 19 | MeO | MeO | NH | $CO_2Me$ | H | 182.0 | 53.8 / 54.1 | 4.8 / 4.9 | 19.3 / 19.2 |
| 20 | MeO | $NEt_2$ | O | $CO_2Me$ | H | oil | 57.8 / 57.7 | 6.1 / 6.1 | 16.9 / 16.4 |
| 21 | MeO | $NHNMe_2$ | O | $CO_2Me$ | H | 160.2 | 52.7 / 52.5 | 5.4 / 5.4 | 21.9 / 21.7 |
| 22 | MeO | NMe(OMe) | O | $CO_2Me$ | H | oil | 52.5 / 53.4 | 5.0 / 5.5 | 17.5 / 16.8 |

TABLE 1-continued

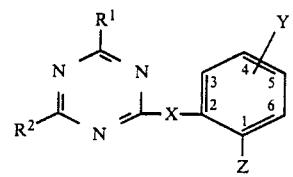
(I')

| Example | R¹ | R² | X | Z | Y | mp (°C.) | Analysis (%) C | H | (Calc. Found) N |
|---|---|---|---|---|---|---|---|---|---|
| 23 | MeO | −O−N=C(CH₃)₂ | O | $CO_2Me$ | H | 88.6 | 54.2 / 54.5 | 4.9 / 5.0 | 16.9 / 16.7 |
| 24 | MeO | MeO | O | $CO_2Me$ | 4,5-CH=CH.CH=CH− | 104.6 | 59.8 / 59.4 | 4.4 / 4.4 | 12.3 / 12.3 |
| 25 | MeO | MeO | O | $CO_2Bz$ | H | 59.8 | 62.1 / 62.8 | 4.6 / 4.7 | 11.4 / 11.8 |
| 26 | MeO | pyrrolidin-1-yl | O | $CO_2Me$ | H | oil | — | — | — |
| 27 | OMe | 2-(CO₂Me)-phenoxy | O | $CO_2Me$ | H |  | 58.2 / 58.3 | 4.2 / 4.3 | 10.2 / 10.1 |
| 28 | OMe | OMe | O | COMe | H | 108.5 | 56.7 / 56.8 | 4.8 / 4.8 | 15.3 / 15.2 |
| 29 | OMe | OMe | O | $CH_2CO_2Me$ | H | 70.6 | 55.1 / 55.3 | 4.9 / 5.0 | 13.8 / 13.7 |
| 30 | NHMe | NHMe | O | $CO_2Me$ | H | 167.0 | 54.0 / 53.9 | 5.2 / 5.3 | 24.2 / 24.4 |
| 31 | OMe | NHEt | O | $CO_2Me$ | H | 104.5 | 55.3 / 55.3 | 5.3 / 5.4 | 18.4 / 18.6 |
| 32 | OMe | OMe | O | $CO_2Me$ | 6-OH | 103.5 | 51.0 / 50.7 | 4.3 / 4.4 | 13.7 / 14.0 |
| 33 | OMe | OMe | O | $CO_2Me$ | 6-O-(4,6-dimethoxy-1,3,5-triazin-2-yl) | 148.9 | 48.4 / 48.8 | 4.1 / 4.1 | 18.8 / 18.5 |
| 34 | OMe | $NMe_2$ | O | $CO_2CH_2Ph$ | H | oil | — | — | — |
| 35 | OMe | NHMe | O | $CO_2CH_2Ph$ | H | 97–98 | 62.3 / 62.3 | 4.9 / 4.9 | 15.3 / 15.4 |
| 36 | OMe | N(Me)OMe | O | $CO_2CH_2Ph$ | H | Oil | — | — | — |
| 37 | OMe | OMe | O | $CO_2Me$ | 5,6-benzo | 191.0 | 59.8 / 59.7 | 4.4 / 4.5 | 12.3 / 12.3 |
| 38 | OMe | OMe | O | $CO_2Me$ | 3-Cl | 108.0 | 47.9 / 48.4 | 3.7 / 3.8 | 12.9 / 12.7 |
| 39 | OMe | OMe | O | $CO_2CH=CH_2$ | H | 55.6 | 55.5 / 55.3 | 4.3 / 4.4 | 13.9 / 13.9 |
| 40 | OMe | OMe | O | $CO_2$-(4-chlorophenyl) | H | 108.1 | 55.7 / 55.8 | 3.6 / 3.7 | 10.8 / 10.8 |
| 41 | OMe | OMe | O | $CO_2^iPr$ | H | 49.5 | 56.4 / 56.2 | 5.3 / 5.4 | 13.2 / 13.0 |

TABLE 1-continued (I')

$$\text{structure with } R^1, R^2, X, Y, Z \text{ substituents on triazine-phenyl}$$

| Example | $R^1$ | $R^2$ | X | Z | Y | mp (°C.) | Analysis (%) C | H | (Calc. Found) N |
|---|---|---|---|---|---|---|---|---|---|
| 42 | OMe | morpholino (—N(CH$_2$CH$_2$)$_2$O) | O | CO$_2$CH$_2$Ph | H | 64–65 | 62.6 / 62.5 | 5.2 / 5.2 | 13.3 / 13.4 |
| 43 | OMe | NEt$_2$ | O | CO$_2$CH$_2$Ph | H | Oil | 64.7 / 65.2 | 5.9 / 6.0 | 13.7 / 13.6 |
| 44 | OMe | 2-(CO$_2$CH$_2$Ph)phenoxy | O | CO$_2$CH$_2$Ph | H | Oil | — | — | — |
| 45 | OMe | NHCH$_2$CF$_3$ | O | CO$_2$CH$_2$Ph | H | 127.5–129 | 55.3 / 54.2 | 3.9 / 4.1 | 12.9 / 12.5 |
| 46 | Cl | NH$_2$ | O | CO$_2$CH$_2$Ph | H | 194–196 | 57.2 / 57.7 | 3.7 / 4.0 | 15.7 / 15.9 |
| 47 | OMe | NH$_2$ | O | CO$_2$CH$_2$Ph | H | 129.0 | 61.4 / 61.7 | 4.6 / 4.8 | 15.9 / 15.6 |
| 48 | OMe | OMe | O | menthyloxycarbonyl (CO$_2$-menthyl) | H | Oil | 63.6 / 63.6 | 7.0 / 7.5 | 10.1 / 10.2 |
| 49 | OMe | OMe | O | CO$_2$Me | 4-OMe | 102–104 | 52.3 / 51.6 | 4.7 / 4.8 | 13.1 / 12.9 |
| 50 | OMe | OMe | O | CO$_2$Ph | 3,4-naphtho (fused naphthalene) | 204–205 | — | — | — |
| 51 | OMe | OMe | O | CO$_2$Me | 5-NO$_2$ | 114–115 | 46.4 / 45.9 | 3.6 / 3.6 | 16.7 / 16.6 |
| 52 | OMe | 2-methylphenoxy | O | CO$_2$CH$_2$Ph | H | Oil | 67.7 / 66.5 | 4.8 / 5.1 | 9.5 / 9.4 |
| 53 | OMe | NHOMe | O | CO$_2$CH$_2$Ph | H | 96–98 | 59.7 / 59.9 | 4.7 / 4.8 | 14.7 / 14.8 |
| 54 | OMe | OMe | O | CO$_2$Me | 5-CHO | 87.0–87.5 | 52.7 / 52.8 | 4.2 / 4.2 | 13.2 / 13.3 |
| 55 | OMe | OMe | O | CHO | 4-NEt$_2$ | 97 | 57.8 / 57.9 | 6.0 / 6.1 | 16.9 / 17.0 |
| 56 | OMe | OCH$_2$CF$_3$ | O | CO$_2$CH$_2$Ph | H | 86.0–86.5 | 55.2 / 55.3 | 3.7 / 3.8 | 9.7 / 10.0 |
| 57 | OMe | Cl | O | CO$_2$CH$_2$Ph | H | 73–74 | 58.2 / 58.6 | 3.8 / 4.0 | 11.3 / 11.1 |
| 58 | OMe | OMe | O | CO$_2$CH$_2$Ph | H | 97–98 | 64.5 / 64.3 | 4.4 / 4.4 | 10.8 / 10.6 |
| 59 | OMe | OMe | O | CO$_2$Me | 3-Ph | 148–149 | 62.1 / 62.6 | 4.6 / 4.6 | 11.5 / 11.3 |
| 60 | OMe | OMe | O | CO$_2$Me | 6-Cl | 63 | 47.9 / 48.2 | 3.7 / 3.9 | 12.9 / 13.5 |

EXAMPLE 61

2-(4,6-Dimethoxy-1,3,5-triazin-2-yl)oxy benzoic acid

The phenyl ester of Example 14 (1.77 g) was added to a stirred solution of sodium hydroxide in a 1:1 mixture of tetrahydrofuran and water (50 ml) at pH 9 to 10. After stirring overnight, the mixture was poured into water (300 ml) and neutralised with dilute hydrochloric acid. The product was extracted into ether (3×100 ml) and the combined organic phase dried using anhydrous magnesium sulphate and evaporated to yield the title compound (0.2 g), which after recrystallisation from ethyl acetate/hexane had mp 151.6° C.

Analysis (%): Calc. C 52.0, H 4.0, N 15.2. Found C 51.9, H 4.0, N 14.4.

EXAMPLE 62

Methyl 2-(4,6-dimethoxy-1,3,5-triazin-2-yl) sulphonyl benzoate

A solution of m-chloroperbenzoic acid (1.73 g) in dichloromethane (20 ml) was added to a stirred solution of the sulphide compound of Example 18 (1.54 g) in dichloromethane (30 ml) at 0° C. The reaction was warmed to room temperature and stirred for 1 hour and then refluxed for 16 hours. Water (50 ml) was added and the aqueous phase extracted with dichloromethane. After washing and drying of the organic phase (using anhydrous magnesium sulphate) and evaporation in vacuo there was obtained the title compound (1.05 g), m.p. 143.6° C.

Analysis (%): Calc. C 46.0, H 3.8, N 12.4. Found C 46.1, H 3.9, N 12.3.

EXAMPLE 63

Methyl N-methyl[2-(4,6-dimethoxy-1,3,5-triazin-2-Yl)]amino benzoate

The aminotriazine of Example 19 (1.45 g) in dry dimethyl formamide (30 ml) was treated with potassium t-butoxide (0.78 g). Methyl iodide (1.42 g) was added to the stirred mixture. After stirring for 2 hours, water (100 ml) was added and the products extracted into ether. The organic phase was washed with water, dried, using anhydrous magnesium sulphate, evaporated in vacuo, and flash chromatographed to give the title compound (0.93 g) mp. 88.3° C.

Analysis (%): Calc. C 55.3, H 5.3, N 18.4. Found C 55.3, H 5.0, N 18.4.

EXAMPLE 64

S-n-Propyl 2-(4,6-dimethoxy-1,3,5-triazin-2-yl)oxy thiobenzoate

To a stirred suspension of the acid of Example 61 (2.77 g) in dry dichloromethane (50 ml), were added 4-dimethylaminopyridine (100 mg) and 1-propanethiol (3 ml). 2.3 g of dicyclohexylcarbodiimide were added to the reaction mixture and stirring was continued for 2 hours at room temperature. The reaction mixture was filtered and the filtrate subjected to evaporation. The residue was taken up in ether and the mixture filtered to remove further insoluble material. The ether solution was washed twice with 0.5N HCl and with a saturated sodium bicarbonate solution. After drying over magnesium sulphate and evaporation 1.4 g of the title compound was obtained. mp: 59.5° C.

Analysis (%): Calc. C 53.7, H 5.1, N 12.5. Found C 53.6, H 5.2, N 12.7.

EXAMPLE 65

Sodium 2-(4,6-dimethoxy-1,3,5-triazin-2-yl)oxy benzoate

The acid of Example 61 (1.5 g) was added to a stirred solution of sodium bicarbonate (0.43 g) in water (50 ml). Stirring was continued and the mixture heated to 50° C. for 1 hour. After cooling to room temperature, the insoluble material that had formed was filtered off and the solution evaporated to dryness. 1.45 g of the title compound was obtained. mp: 188° C.

Analysis (%): Calc. C 48.2, H 3.4, N 14.0. Found C 47.4, H 3.3, N 13.3.

EXAMPLE 66

2-(6-methoxy-4-dimethylamino-1,3,5-triazin-2-yl)oxy benzoic acid

The compound of Example 34 (4.45 g) was taken up in ethanol and palladium/charcoal powder added. The ester was reduced by hydrogenation at room temperature and pressure. The catalyst was filtered off and the solvent removed to yield a white crystalline product. After recrystallisation, 2.2 g of the title compound was obtained. mp 148.5°–149° C.

Analysis (%): Calc. C 53.8, H 4.8, N 19.3. Found C 54.5, H 5.0, N 19.7.

Example 67

Methyl 2-(6-methoxy-1,3,5-triazin-2-yl)oxy benzoate

The methyl benzoate of Example 2 (2.96 g) was dissolved in ethylacetate and triethylamine and 5% by weight palladium on charcoal was added. The mixture was then subject to hydrogenation for 2 hours at room temperature and pressure. After removal of the catalyst and solvent, 0.56 g of the title compound was obtained as an oil.

Analysis (%): Calc. C 55.2, H 4.2, N 16.1. Found C 54.9, H 4.2, N 15.9.

The following further compounds of general formula I set out in Table 2 below were made using similar methods to those described in Examples 64 and 66 above.

TABLE 2

| Example | $R^1$ | $R^2$ | X | Z | Y | mp (°C.) | Analysis (%) C | H | (Calc. Found) N |
|---|---|---|---|---|---|---|---|---|---|
| 68 | OMe | OMe | O | COSPh | H | 114.0 | 58.5 / 58.4 | 4.1 / 4.1 | 11.4 / 11.4 |
| 69 | OMe | OMe | O | COON=< | H | 120.0 | 54.2 / 54.4 | 4.9 / 4.9 | 16.9 / 16.8 |
| 70 | OMe | OMe | O | $CO_2(CH_2)_2OEt$ | H | 69.5 | 55.0 / 55.2 | 5.5 / 5.5 | 12.0 / 12.1 |

TABLE 2-continued

| Example | R¹ | R² | X | Z | Y | mp (°C.) | Analysis (%) C | H | (Calc. Found) N |
|---|---|---|---|---|---|---|---|---|---|
| 71 | OMe | NMe$_2$ | O | CO$_2$CH$_2$-[thiophene] | H | 113.0 | 56.0 / 56.4 | 4.7 / 4.7 | 14.5 / 14.2 |
| 72 | OMe | NHMe | O | CO$_2$H | H | 144–145 | 52.2 / 53.0 | 4.4 / 4.6 | 20.3 / 20.2 |

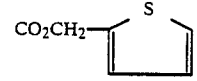

EXAMPLE 73

Herbicidal Activity

To evaluate their herbicidal activity, compounds according to the invention were tested using as representative range of plants: maize, *Zea mays* (Mz); rice, *Oryza sativa* (R); barnyard grass, *Echinochloa crusgalli* (BG); oat, *Avena sativa* (O); linseed, *Linum usitatissimum* (L); mustard, *Sinapsis alba* (M); sugar beet, *Beta vulgaris* (SB) and soya bean, *Glycine max* (S).

The tests fall into two categories, pre-emergence and post-emergence. The pre-emergence tests involved spraying a liquid formulation of the compound onto the soil in which the seeds of the plant species mentioned above had recently been sown. The post-emergence tests involved two types of test, viz., soil drench and foliar spray tests. In the soil drench tests the soil in which the seedling plants of the above species were growing was drenched with a liquid formulation containing a compound of the invention, and in the foliar spray tests the seedling plants were sprayed with such a formulation.

The soil used in the tests was a prepared horticultural loam.

The formulations used in the tests were prepared from solutions of the test compounds in acetone containing 0.4% by weight of an alkylphenol/ethylene oxide condensate available under the trade mark TRITON X-155. These acetone solutions were diluted with water and the resulting formulations applied at dosage levels corresponding to 5 kg or 1 kg of active material per hectare in a volume equivalent to 600 litres per hectare in the soil spray and foliar spray test, and at a dosage of level equivalent to 10 kilograms of active material per hectare in a volume equivalent to approximately 3,000 liters per hectare in the soil drench tests.

In the pre-emergence tests untreated sown soil and in the post-emergence test untreated soil bearing seedling plants were used as controls.

The herbicidal effects of the test compounds were assessed visually twelve days after spraying the foliage and the soil, and thirteen days after drenching the soil and were recorded on a 0–9 scale. A rating 0 indicates growth as untreated control, a rating 9 indicates death. An increase of 1 unit on the linear scale approximates to a 10% increase in the level of effect.

The results of the tests are set out in the following Table 3 in which the compounds are identified by reference to the preceding examples.

Absence of a numerical value in the Table indicates that 0 rating was obtained.

TABLE 3

| Compound of Ex. No. | Soil drench 10/kg/ha Mz | R | BG | O | L | M | SB | S | Dosage kg/ha | Foliar spray Mz | R | BG | O | L | M | SB | S | Pre-emergence Mz | R | BG | O | L | M | SB | S |
|---|---|---|---|---|---|---|---|---|---|---|---|---|---|---|---|---|---|---|---|---|---|---|---|---|---|
| 1 | 8 | 7 | 8 | 8 | 7 | 8 | 8 | 7 | 5 | 8 | 7 | 8 | 8 | 7 | 8 | 9 | 8 | 9 | 9 | 9 | 8 | 8 | 7 | 8 | 8 |
|   |   |   |   |   |   |   |   |   | 1 | 7 | 7 | 7 | 7 | 7 | 7 | 8 | 8 | 9 | 9 | 9 | 7 | 7 | 4 | 8 | 4 |
| 3 | 7 | 6 | 8 | 8 | 2 | 5 | 9 | 7 | 5 | 7 | 7 | 8 | 8 | 5 | 9 | 9 | 8 | 8 | 9 | 8 | 8 | 3 | 7 | 8 | 8 |
|   |   |   |   |   |   |   |   |   | 1 | 7 | 7 | 8 | 7 | 2 | 7 | 8 | 7 | 7 | 9 | 8 | 7 |   | 5 | 8 | 2 |
| 5 | 7 | 8 | 8 | 7 |   | 4 | 4 | 7 | 5 | 4 | 6 | 8 | 7 | 7 | 5 | 8 | 7 | 8 | 8 | 7 | 3 | 4 | 7 |   | 1 |
|   |   |   |   |   |   |   |   |   | 1 | 3 | 4 | 6 | 5 | 2 | 2 | 8 | 2 | 4 | 5 | 7 | 4 |   |   | 5 |   |
| 6 | 7 | 7 | 7 | 7 | 4 | 4 | 8 | 7 | 5 | 7 | 7 | 7 | 7 | 7 | 8 | 8 | 7 | 8 | 9 | 8 | 8 | 5 | 4 | 8 | 2 |
|   |   |   |   |   |   |   |   |   | 1 | 5 | 7 | 7 | 7 | 4 | 5 | 7 | 3 | 8 | 8 | 8 | 7 |   | 2 | 6 |   |
| 7 | 7 | 7 | 7 | 7 | 4 | 7 | 7 | 6 | 5 | 7 | 7 | 8 | 7 | 6 | 7 | 8 | 6 | 8 | 8 | 8 | 7 | 5 | 6 | 8 |   |
|   |   |   |   |   |   |   |   |   | 1 | 6 | 7 | 8 | 6 | 3 | 5 | 8 | 6 | 6 | 8 | 8 | 7 |   | 5 | 6 |   |
| 8 |   |   |   |   |   |   |   |   | 5 | 2 |   | 2 | 1 |   | 2 | 1 | 3 |   |   |   |   |   |   |   |   |
|   |   |   |   |   |   |   |   |   | 1 | 1 |   | 1 | 1 |   | 1 |   |   |   |   |   |   |   |   |   |   |
| 9 |   |   |   |   |   |   |   |   | 5 | 2 | 1 | 1 | 1 | 2 | 3 | 2 | 3 |   |   |   |   |   |   |   |   |
|   |   |   |   |   |   |   |   |   | 1 |   |   |   |   |   |   | 2 | 2 |   |   |   |   |   |   |   |   |
| 10 | 2 |   |   | 2 |   |   | 2 |   | 5 | 2 |   |   | 1 |   | 2 | 6 | 3 |   |   |   |   |   |   |   |   |
|   |   |   |   |   |   |   |   |   | 1 |   |   |   | 1 |   |   | 1 | 2 |   |   |   |   |   |   |   |   |
| 11 |   |   |   |   |   |   | 6 |   | 5 |   |   |   | 2 |   |   | 6 |   |   |   |   |   |   |   |   |   |
|   |   |   |   |   |   |   |   |   | 1 | 1 |   |   | 1 |   |   | 2 |   |   |   |   |   |   |   |   |   |
| 12 | 7 | 8 | 8 | 7 | 4 | 4 | 8 | 7 | 5 | 7 | 7 | 8 | 7 | 5 | 6 | 8 | 6 | 7 | 9 | 8 | 5 | 2 | 4 | 4 |   |
|   |   |   |   |   |   |   |   |   | 1 | 6 | 7 | 8 | 7 | 4 | 5 | 7 | 2 | 4 | 9 | 7 | 1 |   |   |   |   |
| 13 | 8 | 8 | 8 | 8 | 7 | 7 | 8 | 7 | 5 | 8 | 8 | 8 | 8 | 7 | 8 | 9 | 8 | 9 | 9 | 8 | 8 | 7 | 7 | 7 | 6 |
|   |   |   |   |   |   |   |   |   | 1 | 7 | 7 | 8 | 8 | 7 | 7 | 8 | 7 | 8 | 9 | 8 | 8 | 6 | 7 | 7 | 5 |
| 14 | 8 | 8 | 8 | 7 | 7 | 7 | 8 | 7 | 5 | 8 | 8 | 8 | 7 | 7 | 7 | 8 | 7 | 8 | 9 | 9 | 8 | 6 | 6 | 7 | 4 |
|   |   |   |   |   |   |   |   |   | 1 | 7 | 8 | 8 | 7 | 6 | 7 | 8 | 7 | 7 | 9 | 8 | 7 | 5 | 5 | 7 | 4 |
| 15 | 8 | 7 | 8 | 8 |   | 4 | 8 | 4 | 5 | 7 | 7 | 8 | 7 | 3 | 3 | 9 | 3 | 7 | 8 | 8 | 8 |   | 3 | 8 |   |
|   |   |   |   |   |   |   |   |   | 1 | 6 | 5 | 7 | 7 |   |   | 8 | 2 | 5 | 8 | 7 | 7 |   | 1 | 7 |   |
| 16 | 7 | 7 | 7 | 6 |   |   | 7 | 3 | 5 | 5 | 6 | 7 | 6 |   | 4 | 8 | 1 | 4 | 7 | 7 | 6 |   | 2 | 6 |   |
|   |   |   |   |   |   |   |   |   | 1 | 3 | 3 | 6 | 6 |   | 1 | 6 |   | 3 | 6 | 6 | 3 |   | 1 | 5 |   |
| 17 | 6 | 6 | 7 | 4 |   | 6 | 7 | 2 | 5 | 3 | 5 | 7 | 5 | 2 | 8 | 8 | 3 | 4 | 6 | 7 | 6 |   | 6 | 8 |   |
|   |   |   |   |   |   |   |   |   | 1 | 1 | 3 | 5 | 4 |   | 6 | 7 |   | 2 | 3 | 6 | 5 |   | 5 | 6 |   |

TABLE 3-continued

| Compound of Ex. No. | Soil drench 10/kg/ha | | | | | | | | Dosage kg/ha | Foliar spray | | | | | | | | Pre-emergence | | | | | | | |
|---|---|---|---|---|---|---|---|---|---|---|---|---|---|---|---|---|---|---|---|---|---|---|---|---|---|
| | Mz | R | BG | O | L | M | SB | S | | Mz | R | BG | O | L | M | SB | S | Mz | R | BG | O | L | M | SB | S |
| 18 | 7 | 6 | 6 | 5 | 7 | 4 | 8 | | 5 | 7 | 6 | 8 | 7 | 7 | 7 | 8 | 5 | 7 | 7 | 8 | 6 | 7 | 4 | 7 | 4 |
| | | | | | | | | | 1 | 6 | 5 | 6 | 6 | 6 | 6 | 7 | 3 | 5 | 6 | 6 | 4 | 3 | 1 | 6 | |
| 20 | 4 | 4 | 4 | 3 | | | 4 | | 5 | 4 | 4 | 3 | 5 | | | 6 | 3 | 4 | 4 | 3 | 4 | | | | |
| | | | | | | | | | 1 | 1 | 2 | | 4 | | | 2 | 1 | 1 | 1 | | 1 | | | | |
| 21 | 3 | 3 | 4 | 4 | | | 4 | | 5 | | | | 3 | | | 4 | 1 | 4 | 3 | 4 | 3 | | | | |
| | | | | | | | | | 1 | | | | 1 | | | 1 | | 2 | 2 | | 1 | | | | |
| 22 | 5 | 3 | 5 | 6 | | 2 | 3 | | 5 | 6 | 3 | 7 | 7 | | 2 | 5 | 2 | 5 | 4 | 6 | 4 | | | | |
| | | | | | | | | | 1 | 4 | 1 | 3 | 6 | | | | 1 | 2 | 2 | 2 | | | | | |
| 25 | 8 | 8 | 8 | 7 | 4 | 6 | 9 | 8 | 5 | 8 | 7 | 8 | 8 | 7 | 8 | 9 | 8 | 7 | 9 | 8 | 7 | 4 | 6 | 8 | 6 |
| | | | | | | | | | 1 | 7 | 7 | 8 | 8 | 5 | 7 | 9 | 7 | 5 | 8 | 8 | 6 | 2 | 2 | 7 | 5 |
| 31 | 7 | 8 | 7 | 7 | 3 | 7 | 8 | 5 | 5 | 4 | 6 | 6 | 7 | 2 | 5 | 7 | 4 | 7 | * | 7 | 7 | | 7 | 8 | 2 |
| | | | | | | | | | 1 | 2 | 1 | 2 | 5 | | | 2 | 1 | 4 | 5 | 4 | 6 | | | 4 | |
| 32 | | 6 | | | 2 | 3 | 2 | 2 | 5 | 2 | | | | | 2 | 5 | 6 | | | | | | | | |
| | | | | | | | | | 1 | | | | | | | 4 | 4 | | | | | | | | |
| 34 | 7 | 8 | 8 | 8 | | 3 | 8 | 7 | 5 | 8 | 8 | 8 | 8 | 5 | 7 | 9 | 8 | 7 | 9 | 8 | 7 | | 6 | 7 | 6 |
| | | | | | | | | | 1 | 6 | 7 | 8 | 7 | 1 | 5 | 7 | 7 | 5 | 8 | 8 | 6 | | 2 | 6 | 3 |
| 35 | 7 | 8 | 7 | 8 | | 3 | 8 | 5 | 5 | 7 | 7 | 8 | 7 | 5 | 7 | 8 | 8 | 7 | 9 | 8 | 7 | | 4 | 7 | 4 |
| | | | | | | | | | 1 | 5 | 6 | 7 | 6 | | 4 | 7 | 4 | 4 | 8 | 5 | 5 | | 2 | 6 | 3 |
| 36 | 5 | 6 | 6 | 7 | | 2 | 2 | 4 | 5 | 6 | 5 | 7 | 7 | 3 | 5 | 7 | 5 | 4 | 4 | 7 | 6 | | 2 | 2 | 2 |
| | | | | | | | | | 1 | 4 | 2 | 7 | 6 | | | 2 | 3 | 2 | 3 | | 3 | 3 | | 1 | |
| 37 | | | | | | | | | 5 | 2 | | | | | | 6 | 2 | 2 | | | | | | 5 | | |
| | | | | | | | | | 1 | | | | | | | 5 | | | | | | | 2 | | |
| 38 | 7 | 8 | 8 | 7 | 5 | 8 | 8 | 4 | 5 | 5 | 7 | 7 | 7 | 6 | 8 | 9 | 7 | 7 | * | 8 | 7 | 5 | 7 | 8 | 3 |
| | | | | | | | | | 1 | 2 | 6 | 7 | 7 | 2 | 6 | 8 | 6 | 4 | * | 6 | 6 | 2 | 2 | 7 | 1 |
| 39 | 7 | 7 | 8 | 7 | 7 | 7 | 8 | 6 | 5 | 7 | 7 | 8 | 8 | 7 | 8 | 9 | 7 | 9 | 9 | 8 | 8 | 8 | 7 | 8 | 8 |
| | | | | | | | | | 1 | 6 | 7 | 7 | 7 | 6 | 8 | 8 | 7 | 8 | 9 | 8 | 7 | 5 | 6 | 7 | 3 |
| 40 | 7 | 7 | 8 | 7 | 7 | 7 | 8 | 7 | 5 | 7 | 7 | 7 | 7 | 6 | 7 | 8 | 7 | 8 | 9 | 8 | 7 | 4 | 5 | 7 | 5 |
| | | | | | | | | | 1 | 5 | 6 | 7 | 6 | 5 | 6 | 8 | 6 | 5 | 8 | 6 | 7 | 3 | 1 | 7 | 2 |
| 41 | 6 | 7 | 8 | 7 | 7 | 7 | 8 | 7 | 5 | 7 | 6 | 8 | 8 | 8 | 7 | 8 | 7 | 5 | 8 | 8 | 7 | 4 | 5 | 8 | 7 |
| | | | | | | | | | 1 | | 6 | 7 | 7 | 7 | 7 | 6 | 7 | 4 | 8 | 7 | 6 | 2 | 3 | 7 | 4 |
| 43 | | | | | | | | | 5 | 5 | | 3 | 2 | 5 | | 4 | | | | | | | | | |
| | | | | | | | | | 1 | 3 | | 1 | | | | 1 | | | | | | | | | |
| 48 | 4 | | | | | | | | 5 | 5 | 2 | 7 | 6 | 3 | | 6 | 3 | 3 | | 4 | | 4 | | 3 | 3 |
| | | | | | | | | | 1 | 2 | | 4 | 4 | 1 | | 4 | | 1 | | | | | | | |
| 51 | 6 | 3 | 4 | 5 | 3 | 4 | 3 | | 5 | 4 | 4 | 8 | 5 | 3 | 8 | 4 | 3 | 3 | 3 | 6 | 6 | | 6 | 3 | |
| | | | | | | | | | 1 | | | | 2 | 1 | | | | 1 | | 4 | 1 | | 4 | | |
| 53 | 5 | 4 | 4 | 5 | 3 | 4 | 3 | | 5 | 6 | 3 | 7 | 6 | 4 | 6 | 5 | 4 | 8 | 5 | 6 | 3 | | 3 | 3 | 3 |
| | | | | | | | | | 1 | 4 | 1 | 6 | 2 | 2 | 4 | 4 | 3 | 4 | 2 | 3 | 1 | | 2 | 1 | 1 |
| 54 | | | | | | | | | 5 | | | 5 | 3 | | 4 | 5 | 2 | | | | | | | | |
| | | | | | | | | | 1 | | | | 1 | | | 1 | 1 | 2 | | | | | | | |
| 56 | 3 | 3 | 2 | 2 | | 4 | 5 | | 5 | | | | 5 | | 4 | 4 | 2 | | | | | | | 4 | |
| | | | | | | | | | 1 | | | | 3 | | 2 | 2 | | | | | | | | 2 | |
| 58 | 3 | | 4 | 2 | 2 | 2 | 6 | | 5 | 5 | 2 | 6 | 6 | 4 | 2 | 5 | 4 | 2 | 4 | 7 | 2 | 2 | | | |
| | | | | | | | | | 1 | 3 | | 2 | 5 | 1 | | 3 | | | | 2 | | | | | |
| 60 | 7 | 5 | 4 | 7 | | 7 | 4 | | 5 | 7 | 4 | 2 | 5 | 2 | 8 | 6 | 7 | 8 | 9 | 6 | 7 | 3 | 6 | 4 | 7 |
| | | | | | | | | | 1 | 6 | | | 3 | | 6 | 4 | 4 | 7 | 7 | 3 | 6 | | 4 | | 3 |
| 61 | 7 | 7 | 8 | 7 | 7 | 7 | 8 | 7 | 5 | * | * | * | * | * | * | * | * | * | * | * | * | * | * | * | * |
| | | | | | | | | | 1 | 7 | 6 | 8 | 7 | 7 | 7 | 8 | 7 | 8 | 9 | 8 | 7 | 5 | 6 | 7 | 7 |
| 63 | | | | | | | | | 5 | 2 | | 2 | 2 | 2 | 3 | 2 | 2 | | | | | | | | |
| | | | | | | | | | 1 | 1 | | | 1 | | | 1 | | | | | | | | | |
| 64 | 8 | 8 | 8 | 7 | 3 | 4 | 8 | 6 | 5 | 7 | 7 | 8 | 8 | 7 | 7 | 7 | 7 | 7 | * | 8 | 7 | 5 | 7 | 8 | 3 |
| | | | | | | | | | 1 | 7 | 7 | 8 | 7 | 6 | 7 | 7 | 7 | 5 | * | 8 | 6 | 2 | 4 | 7 | 2 |
| 65 | 8 | 8 | 8 | 7 | 7 | 7 | 8 | 7 | 5 | 7 | 7 | 8 | 7 | 8 | 7 | 8 | 7 | 9 | * | 8 | 7 | 7 | 7 | 8 | 7 |
| | | | | | | | | | 1 | 7 | 7 | 8 | 7 | 6 | 7 | 8 | 7 | 8 | * | 8 | 7 | 3 | 5 | 7 | 2 |
| 66 | 7 | 7 | 7 | 8 | 5 | 7 | 8 | 5 | 5 | 7 | 7 | 7 | 7 | 3 | 8 | 8 | 7 | 8 | 9 | 8 | 7 | 6 | 6 | 8 | 7 |
| | | | | | | | | | 1 | 6 | 6 | 7 | 6 | | | 8 | 6 | 7 | 8 | 8 | 7 | 4 | 6 | 7 | 5 |
| 67 | | | | | | | 4 | | 5 | | | | | | | 2 | 4 | | | | | | | | |
| | | | | | | | | | 1 | | | | | | | | 1 | | | | | | | | |
| 68 | 7 | 7 | 8 | 6 | 4 | 5 | 9 | 5 | 5 | 7 | 7 | 8 | 7 | 7 | 7 | 9 | 7 | 6 | 7 | 8 | 5 | | | 8 | 4 |
| | | | | | | | | | 1 | 5 | 6 | 7 | 5 | 4 | 4 | 8 | 5 | 4 | 5 | 5 | 4 | | | 7 | 2 |
| 69 | 8 | 7 | 8 | 7 | 7 | 8 | 9 | 6 | 5 | 8 | 7 | 8 | 7 | 8 | 8 | 8 | 8 | 9 | 9 | 9 | 7 | 8 | 8 | 8 | 8 |
| | | | | | | | | | 1 | 7 | 7 | 8 | 7 | 6 | 7 | 8 | 7 | 9 | 9 | 8 | 7 | 6 | 7 | 7 | 7 |
| 70 | 8 | 7 | 8 | 7 | 7 | 8 | 9 | 6 | 5 | 8 | 7 | 8 | 7 | 7 | 8 | 8 | 6 | 8 | 9 | 8 | 7 | 7 | 8 | 8 | 8 |
| | | | | | | | | | 1 | 7 | 7 | 8 | 7 | 6 | 7 | 8 | 6 | 8 | 9 | 8 | 7 | 4 | 7 | 8 | 7 |
| 71 | 7 | 7 | 8 | 6 | | 6 | 8 | 3 | 5 | 7 | 7 | 8 | 6 | 4 | 7 | 8 | 7 | 8 | 9 | 8 | 7 | 2 | 4 | 6 | 5 |
| | | | | | | | | | 1 | 6 | 6 | 8 | 6 | | 5 | 7 | 5 | 7 | 8 | 8 | 6 | | 2 | 5 | 1 |
| 72 | 8 | 8 | 8 | 7 | 4 | 5 | 8 | 4 | 5 | 8 | 8 | 8 | 7 | 5 | 7 | 8 | 4 | 9 | 9 | 9 | 7 | 5 | 6 | 8 | |
| | | | | | | | | | 1 | 6 | 7 | 7 | 6 | 4 | 4 | 5 | 3 | 8 | 9 | 8 | 5 | 2 | 5 | 7 | |

We claim:

1. A compound of the formula I

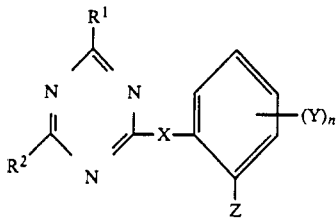

wherein

R$^1$ and R$^2$ each independently represent a hydrogen or halogen atom, or an optionally substituted C$_{1-12}$ alkyl, C$_{2-12}$ alkenyl, C$_{2-12}$ alkynyl, C$_{3-8}$ cycloalkyl, C$_{1-12}$ alkoxy, C$_{2-12}$ alkenyloxy, C$_{2-12}$ alknyloxy, phenyloxy, C$_{1-12}$ alkylthio, C$_{2-12}$ alkenylthio, C$_{2-12}$ alkynylthio, phenylthio or amino group, or a formyl, optionally substituted C$_{1-12}$ alkylcarbonyl, cyano, carboxy, optionally substituted C$_{1-12}$ alkoxycarbonyl, dialkylaminoxy, dialkyliminoxy or azido group;

X represents an oxygen or sulphur atom or a group —SO$_2$—, —SO— or —NR$^4$— where R$^4$ represents a hydrogen atom or an optionally substituted alkyl group;

n is an integer from 1 to 4;

Y represents a hydrogen atom or each Y independently represents a halogen atom, a hydroxy group or an optionally substituted C$_{1-12}$ alkyl, C$_{2-12}$ alkenyl, C$_{2-12}$ alkynyl, phenyl, C$_{1-12}$ alkoxy, C$_{2-12}$ alkenyloxy, C$_{2-12}$ alkynyloxy, phenyloxy, C$_{1-12}$ alkythio, C$_{2-12}$ alkenylthio C$_{2-12}$ alkynylthio, phenylthio or amino group, or a formyl, optionally substituted alkylcarbonyl, cyano or nitro group, or, when n is at least 2, two groups Y may be linked to form a fused saturated carbocyclic ring; and Z represents a hydroxyalkyl, hydroxybenzyl, or mono-, di- or trialkoxyalkyl group, a group —CH=NOH, or an optionally esterified carboxyalkyl group, or a group COR$^3$ where R$^3$ represents a hydrogen or halogen atom, or a hydroxy group, or an optionally substituted C$_{1-12}$ alkyl, phenyl, C$_{2-12}$ alkenyl, C$_{2-12}$ alkynyl, C$_{1-12}$ alkoxy, C$_{2-12}$ alkenyloxy, C$_{2-12}$ alkynyloxy, cycloalkyloxy, phenyloxy, dialkylaminoxy, dialkyliminoxy, amino, C$_{1-12}$ alkylthio, phenylthio, C$_{2-12}$ alkenylthio or C$_{2-12}$ alkynylthio group, or a carboxylic acid salt of a compound of formula I with an equivalent amount of an inorganic or organic cation, said optional substituents for alkyl, alkenyl, alkynyl, alkoxy, alkenylthio, alkylcarbonyl, and alkoxycarbonyl groups being independently selected from one or more of halogen, C$_{1-12}$ alkoxy, hydroxy, C$_{1-12}$ alkylthio, phenylthio, phenyl, alkylsulphinyl, alkylenedioxy, alkylenedithio, haloalkyl, and alkoxycarbonyl groups, thienyl groups and dialkyliminoxy, optionally substituted amino, trialkylsilyl, alkylcarbonyl, phenylcarbonyl, alkoxycarbonyl, carboxy, cyano, thiocyanate, and optionally substituted aminocarbonyl groups, said optional substitutents for phenyl, cycloalkyl, phenyloxy or phenylthio groups may be independently selected from one or more of halogen atoms and nitro, cyano, C$_{1-12}$ alkyl, C$_{1-12}$ haloalkyl, C$_{1-12}$ alkoxy, C$_{1-12}$ alkylthio, C$_{1-12}$ alkoxycarbonyl and aralkoxycarbonyl groups, said optional substitutents for an amino group being independently selected from C$_{1-12}$ alkyl, C$_{1-12}$ alkoxy, amino, mono or dialkylamino, arylamino, alkoxyalkyl, haloalkyl, hydroxy, hydroxyalkyl, carboxyalkyl or alkylcarbonylamino, or the amino group may form part of a pyrrolidinyl or morpholino ring.

2. A compound according to claim 1, wherein R$^1$ and R$^2$ are each independently selected from optionally substituted, C$_{1-4}$ alkyl, C$_{2-4}$ alkenyl, C$_{2-4}$ alkynyl, C$_{1-4}$ alkoxy, C$_{2-4}$ alkenyloxy, C$_{2-4}$ alkynyloxy, C$_{1-4}$ alkylthio groups, C$_{2-4}$ alkenylthio, C$_{2-4}$ alkynylthio, substituted amino groups and di(C$_{1-4}$)alkylaminoxy groups.

3. A compound according to claim 1 or 2 wherein X represents an oxygen or sulphur atom.

4. A compound according to claim 1 or 2 wherein Z represents a group COR$^3$ in which R$^3$ represents a hydrogen atom, a hydroxy group, or an optionally substituted C$_{1-4}$ alkoxy, C$_{2-4}$ alkenyloxy, C$_{2-4}$ alkynyloxy, C$_{1-4}$ alkylthio, C$_{2-4}$ alkenylthio, C$_{2-4}$ alkynylthio phen(C$_{1-4}$)alkoxy, phen(C$_{1-4}$)alkylthio, phenoxy, phenylthio, or di(C$_{1-4}$)alkyliminoxy group.

5. A compound according to claim 1 or 2 wherein n is one and Y represents a hydrogen or halogen atom or an optionally substituted C$_{1-4}$ alkyl, C$_{2-4}$ alkenyl, C$_{2-4}$ alkynyl, phenoxy, phenylthio, phen(C$_{1-4}$)alkoxy, phen(C$_{1-4}$)alkylthio group, a nitro or cyano group, or an amino or substituted amino group.

6. A compound according to claim 1 wherein the compound of the formula I is in the form of a carboxylic acid salt.

7. A herbicidal composition which comprises an effective amount of a herbicidal compound as defined in claim 1 together with a carrier.

8. A method of combating undesired plant growth at a locus comprising treating the locus with an effective amount of a composition as defined in claim 7.

9. A method of combating undesired plant growth at a locus comprising treating the locus with an effective amount of a compound as defined in claim 1.

* * * * *